(12) United States Patent
Wei et al.

(10) Patent No.: US 7,803,568 B2
(45) Date of Patent: Sep. 28, 2010

(54) CARBODITHIOATE LIGANDS FOR NANOTECHNOLOGY AND BIOSENSING APPLICATIONS

(75) Inventors: Alexander Wei, West Lafayette, IN (US); Yan Zhao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 498 days.

(21) Appl. No.: 11/407,751

(22) Filed: Apr. 20, 2006

(65) Prior Publication Data
US 2006/0240489 A1 Oct. 26, 2006

Related U.S. Application Data

(60) Provisional application No. 60/673,190, filed on Apr. 20, 2005.

(51) Int. Cl.
G01N 33/53 (2006.01)
G01N 33/552 (2006.01)
G01N 33/24 (2006.01)
C12M 1/34 (2006.01)

(52) U.S. Cl. .................. 435/7.92; 435/287.2; 436/524; 436/80; 436/81

(58) Field of Classification Search .................. 436/524, 436/80, 81, 120; 977/773
See application file for complete search history.

(56) References Cited

U.S. PATENT DOCUMENTS

| 5,688,998 | A | 11/1997 | Ichimura et al. |
| 6,899,947 | B2 | 5/2005 | Wei et al. |
| 7,030,271 | B2 * | 4/2006 | Wessels et al. ............... 564/155 |
| 2006/0039850 | A1 * | 2/2006 | Jun et al. .................. 423/561.1 |

FOREIGN PATENT DOCUMENTS

| EP | 1215205 A1 * | 6/2002 |
| EP | 1 293 248 A1 | 3/2003 |

OTHER PUBLICATIONS

Jiang et al. Preparation, characterization, and catalytic effect of CS2-stabilized silver nanoparticles in aqueous solution. Langumuir 2001, vol. 17, pp. 3795-3799.*

Michael D. Musick, Christine D. Keating, Melinda, H. Keefe, and Michael J. Natan; *Stepwise Construction of Conductive Au Colliod Multilayers from Solution*; Chem. Mater., vol. 9, No. 7 (1997); pp. 1499-1501.

J. Schmitt, P. Machtle, D. Eck, H. Mohwald, and C.A. Helm; *Preparation and Optical Properties of Colloidal Gold Monolayers*; Langmuir, vol. 15, No. 9 (1999); pp. 3256-3266.

Kenneth R. Brown, Daniel G. Walter, and Michael J. Natan; *Seeding of Colloidal Au Nanoparticle Solutions. 2. Improved Control of Particle Size and Shape*; Chem. Mater., vol. 12, No. 2 (2000); pp. 306-313.

(Continued)

*Primary Examiner*—Shafiqul Haq
(74) *Attorney, Agent, or Firm*—Bose McKinney & Evans LLP

(57) ABSTRACT

The present invention is directed to methods and products related to carbodithioate ligands bonded to surfaces. The invention is further directed to molecular and biomolecular sensing methods based on analyte recognition by carbodithioate ligands bonded to surfaces.

8 Claims, 2 Drawing Sheets

OTHER PUBLICATIONS

Figure 1:
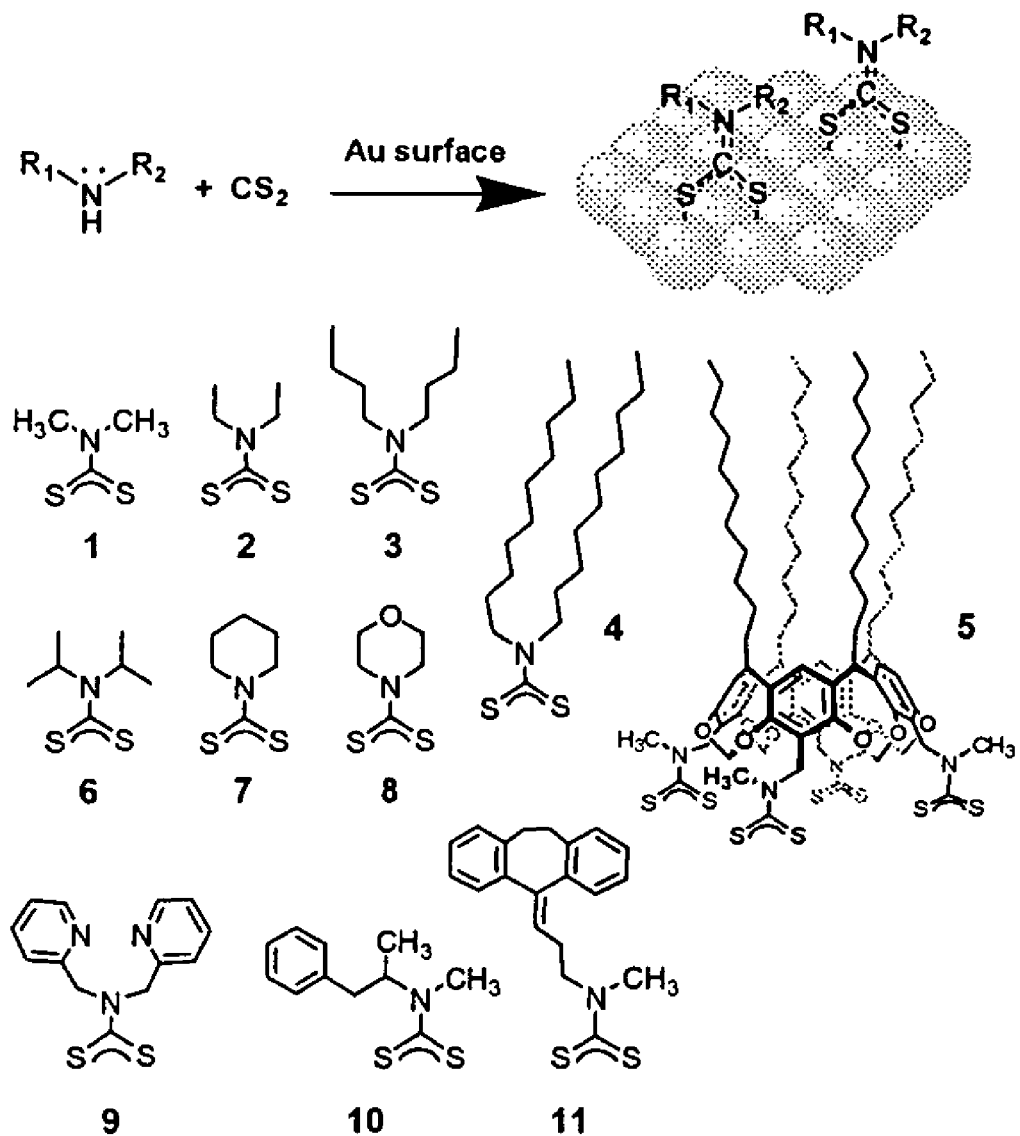

Peter M. Tessier, Orlin D. Velev, Anand T. Kalambur, John F. Rabolt, Abraham M. Lenhoff, and Eric W. Kaler; *Assembly of Gold Nanostructured Films Templated by Colloidal Crystals and Use in Surface-Enhanced Raman Spectroscopy*; J. Am. Chem. Soc., vol. 122, No. 39 (2000); pp. 9554-9555.

Alexander Wei, Beomseok Kim, Bryce Sadtler, and Steven L. Tripp; *Tunable Surface-Enhanced Raman Scattering from Large Gold Nanoparticle Arrays*; Chem. Phys. Chem., No. 12 (2001), 743-745.

R. Balasubramanian, Beomseok Kim. Steven L. Tripp, Xuejun Wang, Marya Lieberman, and Alexander Wei; *Dispersion and Stability Studies of Resorcinarene-Encapsulated Gold Nanoparticles*: Langmuir, vol. 18, No. 9 (2002); pp. 3676-3681 and includes supporting information pp. S1-S5.

Pale-Grosdemange, C.; Simon, E. S.; Prime, K. L.; Whitesides, G. M., "*Formation of Self-Assembled Monolayers by Chemisorption of Derivatives of Oligo (ethylene glycol) of Structure $HS(CH_2)_{11}(OCH_2CH_2)_mOH$ on Gold[1]*", J. Am. Chem. Soc. 1991, vol. 113, pp. 12-20.

Dubois LH, Nuzzo RG., "Synthesis, Structure, and Properties of Model Organic Surfaces", Annu Rev Phys Chem 1992; vol. 43: pp. 437-463.

Allen C. Templeton, W. Peter Wuelfing, and Royce W. Murray, "*Monolayer-Protected Cluster Molecules*", Accts. Chem. Res., 2000, vol. 33, pp. 27-36.

Mirkin CA, Letsinger RL, Mucic RC, Storhof JJ, " *A DNA-based method for nationally assembling nanoparticles into macroscopic materials*", (1996) Nature, vol. 382, pp. 607-609.

A. Paul Alivisatos, Xiaogang Peng, Troy E. Wilson, Kai P. Johnsson, Colin J. Loweth, Marcel P. Bruchez, Jr., and Peter G. Schultz, "*Organization of 'nanocrystal molecules' using DNA*", Nature, (Aug. 15, 1996), vol. 382, pp. 609-611.

He, L.; Musick, M. D.; Nicewarner, S. R.; Salinas, F. G.; Benkovic, S. J.; Natan, M. J.; Keating, C. D. "*Colloidal Au-Enhanced Surface Plasmon Resonance for Ultrasensitive Detection of DNA Hybridization*" J. Am. Chem. Soc. 2000, vol. 122, pp. 9071-9077.

Sun X., Sheardown H., Tengvall P., Brash JL., "*Peptide modified gold-coated polyurethanes as thrombin scavenging surfaces*", J Biomed Mater Res, (2000) vol. 49, pp. 66-78.

A.E. Strong, B.D. Moore, "*Self-assembling monolayers of helical oligopeptides on gold with application sin molecular electronics*", J. Mater. Chem.1999, vol. 9, pp. 1097-1105.

Tkachenko AG, Xie H, Coleman D, Glomm W, Ryan J, Anderson MF, Franzen S, Feldheim DL: "*Multifunctional Gold Nanoparticle-Peptide Complexes for Nuclear Targeting*", J Am Chem Sec 2003, vol. 125. pp. 4700-4701.

P. Pengo, Q. B. Broxterman, B. Kaptein, L. Pasquato, P. Scrimin, "*Synthesis of a Stable Helical Peptide and Grafting on Gold Nanoparticles*", Langmuir, 2003, vol. 19, pp. 2521-2524.

M.C. Fritz, G. Hëhner, N. D. Spencer, R. Bürli, A. Vasella, "*Self-Assembled Hexasaccharides: Surface Characterization of Thiol-Terminated Sugars Adsorbed on a Gold Surface*", Langmuir; 1996, vol. 12(25), pp. 6074-6082.

J.M. de la Fuente, A. G. Barrientos, T.C. Rojas. J. Rojo, J. Cañada, A. Fernández, S. Penadés. "*Gold Glyconanoparticies as Water-Soluble Polyvalent Models to Study Carohydrate Interactions*", Angew. Chem. Int. Ed. Engl., 2001, vol. 40, pp. 2258-2261.

Otsuka, H.; Akiyama, Y.; Nagasaki, Y.; Kataoka, K., "*Quantitative and Reversible Lectin-Induced Associationof Gold Nanoparticles Modified with α-Lactosyl-ω-mercapto-poly(ethylene glycol)*", J. Am. Chem. Soc. 2001, vol. 123, pp. 8226-8230.

B. T. Houseman and M. Mrksich in Host-Guest Chemistry, "*Model Systems for Studying Polyvalent Carbohydrate Binding Interactions*", Topics in Current Chemistry, 2002, vol. 218, pp. 1-44.

Smith, E. A., Thomas, W. D., Kiessling, L. L., and Corn, R. M., "*Surface Plasmon Resonance Imaging Studies of Protein—Carbohydrate Interactions*", J. Am. Chem. Soc. (2003), vol. 125, pp. 6140-6148.

Schlenoff, J. B.; Li, M.; Ly, H. J., "*Stability and Self-Exchange in Alkanethiol Monolayers*", Am. Chem. Soc. 1995, vol. 117, pp. 12528-12536.

Flynn, N. T.; Tran, T. N. T.; Cima, M. J.; Langer, R., "*Long-Term Stability of Self-Assembled Monolayers in Biological Media*", Langmuir 2003, vol. 19, pp. 10909-10915.

Ulman A., "*Formation and Structure of Self-Assembled Monolayers*", Chem Rev. 1996, vol. 96, pp. 1533-1554.

R. Colorado, Jr.; R.J. Viliazana; T.R. Lee, "*Self-Assembled Monolayers on Gold Generated from Aliphatic Dithiocarboxylic Acids*", Langmuir, 1998, vol. 14, pp. 6337-6340.

Querner C, Reiss P, Bleuse J, et al., "*Chelating Ligands for Nanocrystals' Surface Functionalization*", Journal of the American Chemical Society (2004), vol. 126(37). pp. 11574-11582.

Coucouvanis, D., "*The Chemistry of the Dithioacid and 1, 1-Dithiolate Complexes*", Prog. Inorg. Chem. (1970), vol. 11, pp. 233-371.

T. Arndt, H. Schupp, W. Schrepp, "*Self-Assembled and Langmuir-Blodgett Films of Thiocarbaminates: A Comparative Study*", Thin Solid Films 1989, vol. 178, pp. 319-326.

McCubbin, Q. J., Stoddart, F. J., Welton, T., White, A. J. P L., Williams, D. J., "*Dithiocarbamate-Functionalized Dendrimers as Ligands for Metal Complexes*", Innorganic Chemistry (1998), vol. 37, pp. 3753-3758.

Fox,O.D., Drew, M.G.B., Beer,P.D., "*Resorcarene-Based Nanoarchitectures: Metal-Directed Assembly of a Molecular Loop and Tetrahedron*", Angew. Chem.lnt.Ed 2000, vol. 39, pp. 136-140.

Berry, Neil G.; Pratt, Michelle D.; Fox, O. Danny; Beer, Paul D., "*Transition Metal Self-assembly of Dithiocarbamate Based Anion Receptors*", Supramolecular Chemistry (2001), vol. 13(6), pp. 677-682.

Beer. P.D., Berry, N., Drew, M.G.B., Fox, O.D., Padilla-Tosta, M.E., and Patell, S., "*Self-assembled dithiocarbamate-copper(II) macrocycles for electrochemical anion recognition*". J. Chem. Soc. Chem. Commun., 2001, pp. 199-200.

P. D. Beer, N. G. Berry, A. R. Cowley, E. J. Hayes, E. C. Oates, W. W. H. Wong, "*Metal-directed self-assembly of bimetallic dithiocarbamate transition metal cryptands and their binding capabilities*", Chem. Commun. 2003, vol. 19, pp. 2408-2409.

Boerrigter, H., Verboom, W., Reinhoudt, D.N., "*Novel Resorcinarene Cavitand-Based CMP(O) Cation Ligands: Synthesis and Extraction Properties*", Journal of Organic Chemistry 1997, vol. 62, pp. 7148-7155.

Beomseok Kim, R. Balasubramaniam, Waleska Perez-Segarra, Alexander Wei, Björn Decker, and Jochen Mattay, "*Self-Assembly of Resorcinarene-stabilized Gold Nanoparticles: Influence of the Macrocyclic Headgroup*", Supramolecular Chemistry 2005, vol. 17, pp. 173-180.

Gao, P., Gosztola, D., Leung, L.W.H., Weaver, M.J., "*Surface-Enhanced Raman-Scattering At Gold Electrodes-Dependence on Electrochemical Pretreatment Conditions and Comparisons With Silver*", Journal of Electroanalytical Chemistry, 1987, vol. 233, pp. 211-222.

Sanchez-Cortes, S., M. Vasina, O. Francioso, and J.V. Garcia-Ramos, "*Raman and surface-enhanced Raman spectroscopy of dithiocarbamate fungicides*"; Vibrational Spectroscopy, 1998, vol. 17(2), pp. 133-144.

Sanchez-Cortes S, Domingo C, Garcia-Ramos JV, et al., "*Surface-Enhanced Vibrational Study (SEIR and SERS) of Dithiocarbamate Pesticides on Gold Films*", Langmuir (2001), vol. 17(4), pp. 1157-1162.

Demers, L. M., Mirkin, C. A.; Mucic, R. C.; Reynolds, R. A., Letsinger,R. L.; Elghanian, R.; Viswanadham, G. "*A Fluorescence-Based Method for Determining the Surface Coverage and Hybridization Efficiency of Thiol-Capped Oligonucleotides Bound to Gold Thin Films and Nanoparticles*", Anal.Chem., 2000, vol. 72, pp. 5535-5541.

Castelino, K.; Kannan, B.; Majumdar, A., "*Characterization of Grafting Density and Binding Efficiency of DNA and Proteins on Gold Surfaces*"; Langmuir 2005, vol. 21, pp. 1956-1961.

Uppadine, Lindsay H.; Weeks, Jennifer M.; Beer, Paul D., "*Metal-directed self-assembly of terphenyl based dithiocarbamate ligands*"; Journal of the Chemical Society, Dalton Transactions (2001), vol. 22, pp. 3367-3372.

Love JC, Estroff LA, Kriebel JK, et al., "*Self-Assembled Monolayers of Thiolates on Metals as a Form of Nanotechnology*", Chemical Reviews (2005), vol. 105(4), pp. 1103-1169.

Mylrajan, M., "*SERS, FT-Raman and FT-IR studies of dithlocarbamates*", J. Mol. Struct. 1995, vol. 348, pp. 257-260.

Kang, J. S.; Hwang, S. Y.; Lee, C. J.; Lee, M. S., "*SERS of Dithlocarbamate Pesticides Adsorbed on Silver Surface; Thiram*", Bull. Korean Chem. Soc. 2002, vol. 23, pp. 1604-1610.

"*New opportunities from old chemistry in surface science, say Purdue chemists*", Purdue UNS press release, May 26, 2005, (3 pages).

"*Science Concentrates*", C&EN Press Release, May 23, 2005, vol. 83, No. 21 (2 pages).

Wei Research Group—Dow AgroSciences PowerPoint Presentation presented in Zionsville, IN on Mar. 22, 2005. (44 pages).

Y. Zhao, W. Pérez-Segarra, Q. Shi, A. Wei, "*Dithiocarbamate Assembly on Gold: Amines as Replacement Ligands for Thiols [1]*", Abstract, Adv. Supremol. Chem, 2005. (2 pages).

Waleska Pérez-Segarra. Yan Zhao, Alexander We, "*Spontaneous Formation of Dithiocarbamates on Gold Surfaces*", Abstract from the XIIIth international Symposium on Supramolecular Chemistry, University of Notre Dame, South Bend, IN. Jul. 25-30, 2004 (1 page).

Zhao, Y.; Sadtler, B.; Min, L.; Hockerman, G. H.; Wei, A., "*Nanoprobe implantation into mammalian cells by cationic transfection*", Chem. Commun. 2004, pp. 784-785.

Sadtler, B.; Wei, A. "Spherical ensembles of gold nanoparticles on silica: electrostatic and size effects", Chem. Commun., 2002, pp. 1604-1605.

Pérez-Segarra, Waleska, "*Spontaneous Formation of Dithiocarbamate Ligands on Nanostructured AU Surfaces*", Master of Science Thesis presented to Purdue University in Aug. 2004 (114 pages).

* cited by examiner

CARBODITHIOATE LIGANDS FOR NANOTECHNOLOGY AND BIOSENSING APPLICATIONS

This application claims priority to provisional application No. 60/673,190 filed on Apr. 20, 2005.

This invention was made with government support under grant reference numbers NSF CHE-0243496 and ECS-0210445 awarded by the National Science Foundation and EB-00 1777-01 and GM-06982-01 awarded by the National Institutes of Health. The Government has or may have certain rights in the invention.

The present invention relates to methods for preparing carbodithioate ligands bonded to surfaces, methods for biosensing with carbodithioate ligands bonded to surfaces, and carbodithioate ligands.

The functionalization of surfaces with organic ligands has become an important aspect of surface science and nanomaterials chemistry. For example, molecular monolayers are often formed spontaneously by methods, such as the self-assembly of alkanethiols on gold for preparing surfaces, with tunable physical or chemical properties or with molecular recognition elements. Such self-assembled monolayers (SAMs) have potential utility as biosensors for molecules that bind to them such as peptides, small proteins, DNA, carbohydrates, oligonucleotides, and bioactive natural products.

However, SAMs are often limited by their chemical stability. By way of example, thiols, which are often used as the organic ligands for SAMs, can be readily oxidized to disulfides or sulfonates and can desorb or be replaced from the surface by other molecules for being incompatible with other functional groups associated with the ligand. Because they are not sufficiently stable in biological fluids, such thiol-based SAMs have been shown to lack the long-term stability needed for most biomedical applications such as biosensing, which include the use of compounds to detect molecules of biological interest. As such, it would be desirable to have a surface functionalization method that is sufficiently robust for utility in biomedical applications.

The current invention advantageously provides methods for preparing robust carbodithioate ligands bonded to surfaces. Ligands bearing the —$CS_2$ group, for example, have superior chemisorption properties than thiols on a number of surfaces and are more stable in fluids under biologically relevant conditions.

With respect to SAMs that are nanoparticles, metal nanoparticles (e.g., gold nanorods), semiconductor nanoparticles (e.g., CdSe "quantum dot" nanocrystals), and superparamagnetic nanoparticles have excellent potential as site-directed contrast agents in biomedical imaging. The targeted delivery of these nanoparticles to particular regions of the body is dependent on a robust method of surface functionalization, to maintain appropriate levels of biodistribution and to prevent nonspecific cell uptake or protein adsorption. Thiols are inadequate for maintaining stable passivation on metal surfaces, but dithiocarbamates and other carbodithioates are much more robust and will resist surface desorption or displacement under biologically relevant conditions. The robustness of carbodithioate-anchored ligands is also useful for the directed delivery of nanoparticle agents to diseased tissue.

In one aspect of the invention, methods for preparing a surface bonded to a carbodithioate ligand comprising treating the surface with a mixture comprising a nucleophile and a sulfur-containing compound in a suitable solvent are provided.

The invention also relates in one aspect to processes for functionalizing a surface comprising treating a surface bonded to a sulfur atom with a sulfur-bearing compound selected from an isothiocyanate and $R^{20}NCS$, where $R^{20}$ is alkyl, aryl or heteroaryl.

The invention further provides methods for preparing carbodithioate ligands comprising suspending a surface in an aqueous medium and treating the surface with a sulfur-containing compound and a nucleophile.

In yet a further aspect of the invention, carbodithioate ligands alone and bonded with surfaces are provided.

Another aspect of the invention is directed to methods for detecting a molecular or biomolecular analyte using a surface-bound carbodithioate ligand as a recognition element.

Yet another aspect of the invention is directed to methods for functionalizing a surface comprising passivating a surface with a mixture of a carbodithioate ligand not used for molecular recognition and a carbodithioate ligand capable of molecular recognition.

Another aspect of the invention is directed to methods for preparing a core-shell nanomaterial comprising encapsulating a nanomaterial with a carbodithioate ligand; extracting the encapsulated nanomaterial into an organic solvent; and treating with an organometallic compound to form a core-shell nanomaterial.

An additional aspect of the invention is directed to methods for preparing a nanoparticle imaging agent comprising passivating the surface of a nanoparticle and functionalizing the nanoparticle surface with a combination of biologically active nucleophiles and biologically inactive nucleophiles.

Figure 2:
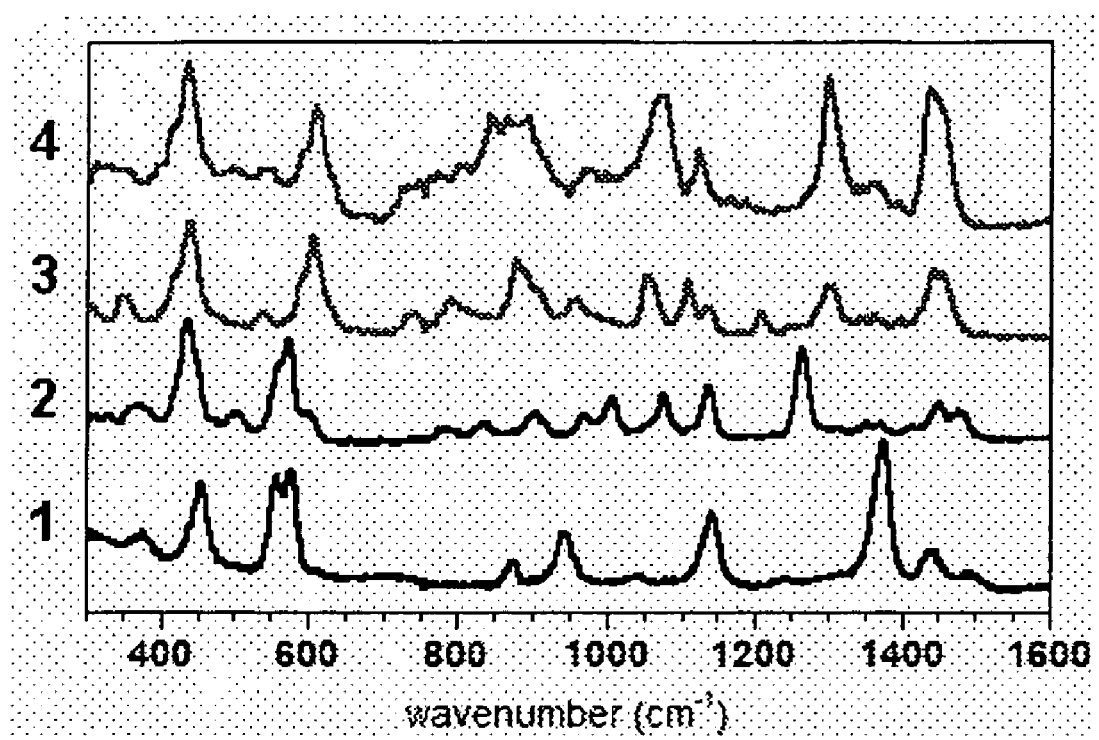

The above-mentioned aspects of the present invention and the manner of obtaining them will become more apparent and the invention itself will be better understood by reference to the following description of the embodiments of the invention taken in conjunction with the accompanying drawings, wherein:

FIG. 1 depicts dithiocarbamate ligands formed on Au surfaces with several exemplary ligand examples in accordance with the present invention; and FIG. 2 depicts selected SERS spectra of dialkyl dithiocarbamates formed on roughened Au surfaces obtained using a dispersive Raman microscope with a 20× objective lens (N.A.=0.4) at an excitation wavelength of 785 nm and an exposure time of 30 seconds in accordance with the present invention.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In one embodiment of the invention, the carbodithioate ligands of the invention are prepared in a mixture of a sulfur-containing compound and a nucleophile in a suitable solvent. It is understood that molecules bearing the carbodithioate ligand may deliver the ligand to the surface. A surface is treated with this mixture by, for example, immersing the surface into the mixture. The carbodithioate ligand may be bonded to the surface by condensing the mixture in the suitable solvent onto the surface. In one preferred embodiment, the approximate molar ratio of the sulfur-containing compound to the nucleophile is 1:1.

In another embodiment of the invention, the sulfur-containing compound is $CS_2$ and is treated with a nitrogen-containing nucleophile to form a carbodithioate ligand bonded to a surface wherein the carbodithioate ligand is selected from $R^1R^2N$—$CS_2$; xanthates; $R^9O$—$CS_2$; $R^{10}SCS_2$; or $R^{11}R^{12}P$ (=O)—CS₂ wherein $R_1$ and $R_2$ are independently selected from —H, alkyl, acyl, aryl, heteroaryl, —$OR^3$, —$NR^4R^5$, $SIR^6R^7R^8$ or $SR^9$;

$R^3$, $R^4$, $R^5$, $R^6$, $R^7$, $R^8$, are independently selected from —H, alkyl, acyl, aryl or heteroaryl;

$R^9$ is aryl or heteroaryl;

$R^{10}$ is alkyl, acyl, aryl, or heteroaryl;

$R^{11}$ and $R^{12}$ are independently selected from alkyl, aryl, —$OR^{13}$, —$NR^{14}R^{15}$, $SiR^{16}R^{17}R^{18}$, or $SR^{19}$;

$R^{13}$, $R^{14}$, $R^{15}$, $R^{16}$, $R^{17}$, $R^{18}$ and $R^{19}$ are independently selected from —H, alkyl, acyl, aryl or heteroaryl.

In an additional embodiment of the invention, a preformed carbodithioate ligand is $R^{20}R^{21}NCS_2$—$S_2CNR^{20'}R^{21'}$ wherein $R^{20'}$ and $R^{21'}$ are independently selected from H, alkyl, acyl, aryl or heteroaryl.

The surface of the invention may be inorganic or metal. A preferred surface is gold. Examples of metals of the invention include Group 13 metals, group 14 metals, and group 15 metals. Other surfaces of the invention include iron oxide, cadmium selenide, cadmium sulfide, and indium tin oxide.

When the surface of the invention is metal, it may be selected from thiophilic metal surfaces including gold, silver, copper, palladium, platinum, and selected steel alloys. A preferred surface is gold.

Surfaces of the invention include nanoparticles. By "nanoparticle" what is meant is a particle having a length in one or more dimensions on the order of 200 nm or less. In one embodiment of the invention, the nanoparticle has a length in one or more dimensions on the order of between about 2 nm to about 100 nm. In another embodiment of the invention, the nanoparticle has a length in one or more dimensions on the order of about 40 nm. Preferred nanoparticles are thiophilic metals and particularly preferred nanoparticles are gold nanoparticles.

When the surface is a nanoparticle, in some embodiments of the invention, the nucleophile encapsulates the nanoparticle during treatment of the nanoparticle with the mixture comprising the sulfur-containing compound and the nucleophile.

For example, aqueous suspensions of approximately 40 nm gold nanoparticles treated with $CS_2$ and the nucleophile tetra (N-methyl)aminomethyl resorcinarene at millimolar concentrations were encapsulated by the resulting carbodithioate ligand. This encapsulation enabled the nanoparticles to be extracted from an aqueous phase into dichloromethane. The ability to be extracted out of the aqueous phase was only seen with encapsulated nanoparticles. No extractions occurred in controls made without $CS_2$ or without tetra (N-methyl)aminomethyl resorcinarene. Examples of nanoparticles capable of being encapsulated include metals, thiophilic semiconductors, and gold.

Nucleophiles of the invention include nitrogen-bearing compounds and sulfur-containing compounds.

Nitrogen-containing nucleophiles of the invention include amines or amides wherein the amines are selected from primary amines, secondary amines, heterocyclic amines, silyl amines or metal salts thereof and the amides are selected from primary amides, secondary amides and metal salt derivatives thereof.

Examples of heterocylic amines include pyrroles, diazoles, triazoles, tetrazoles, pyridones, benzoannulated derivatives, pyrazoles, imidazoles, indoles, benzimidazoles, purines, and metal salt derivatives thereof.

Nitrogen-containing nucleophiles of the invention further include dimethylamine, diethylamine, diisopropylamine, dibutylamine, didecylamine, dipicolylamine, diethanolamine, di(hexaethyleneglycol)amine, morpholine, pyridine, proline and oligopeptides bearing N-terminal prolines, piperazinyl terpyridine, nortriptylene, methamphetamine, reductive amination products of oligosaccharides with primary amines, biotin hydrazide, hexamethyldisilazane, and oligo(ethyleneglycol)diamines conjugated to molecular recognition elements such as folic acid or pteroic acid.

Sulfur-containing compounds which are nucleophiles of the invention include inorganic sulfide, thiols, thioacids, or sulfide-treated surfaces.

Suitable solvents of the invention include aqueous and organic solvents. An example of a preferred suitable organic solvent is an alcohol such as methanol, ethanol, n-propyl alcohol, and isopropyl alcohol.

Carbodithioate ligands of the invention include

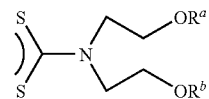

wherein $R^a$ and $R^b$ are independently selected from —H, alkyl, acyl, aryl or heteroaryl. The invention further includes such carbodithioate ligands bonded to surfaces of the invention.

Carbodithioate ligands of the invention further include the structure above with $R^a$ and $R^b$ independently selected from one of the following:

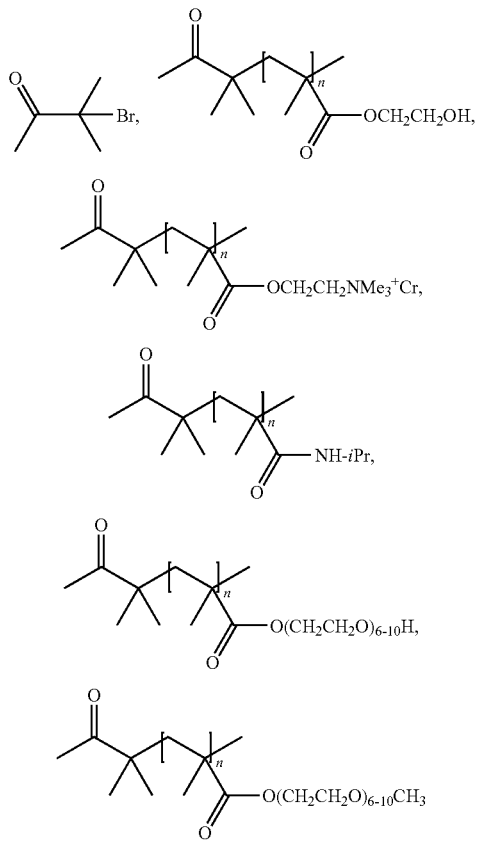

-continued

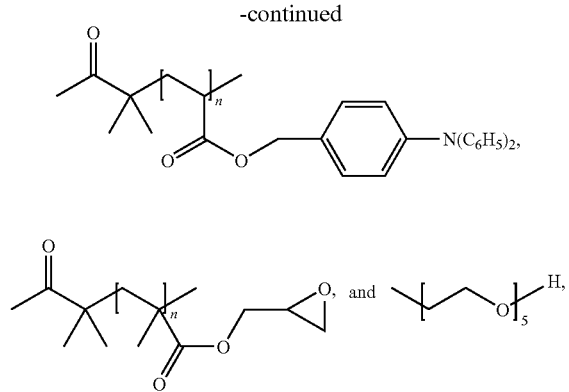

where is an integer from 1 to 99. The invention also includes such carbodithioate ligands bonded to surfaces of the invention.

Carbodithioate ligands of the invention further include the following:

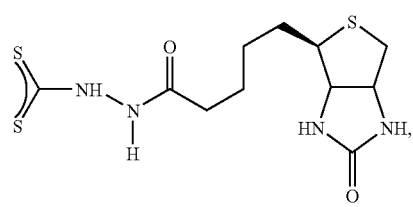

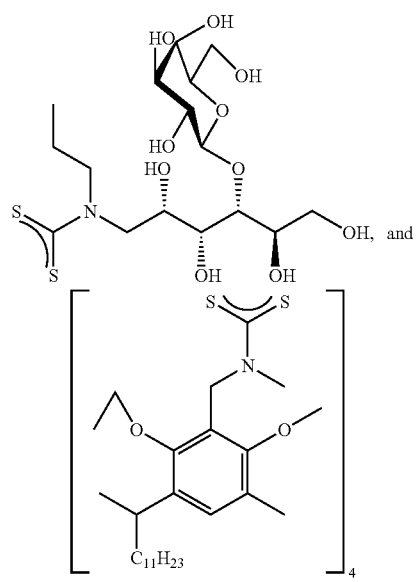

Additional carbodithioate ligands of the invention are ligands having the chemical structure

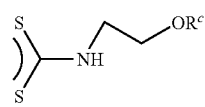

wherein $R^c$ is selected from

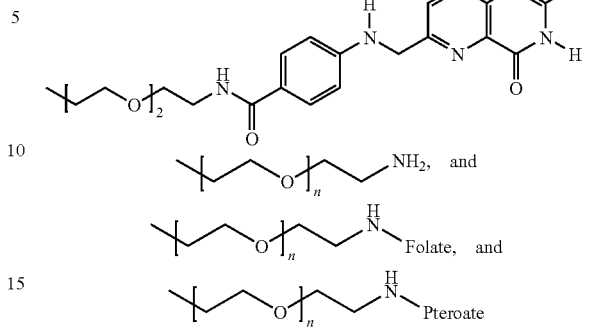

where pteroate is 2-[4-[(2-amino-4-oxo-1H-pteridin-6-yl)methylamino]benzoate], folate is the γ-glutamyl derivative of pteroate, and n=1-99.

Carbodithioate of the invention include ligands having the chemical structure:

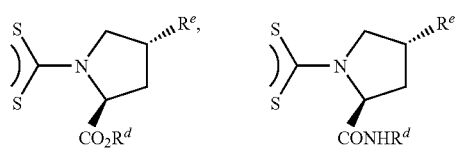

where $R^d$ is selected from $CH_3$, an amino acid, or an oligopeptide, and $R^e$ is selected from hydrogen, OH, alkyl groups, and alkoxyl groups, and the invention also includes surfaces bonded to such ligands.

The ligands of the invention are capable of encapsulating surfaces of the invention in many embodiments. For example, the ligand

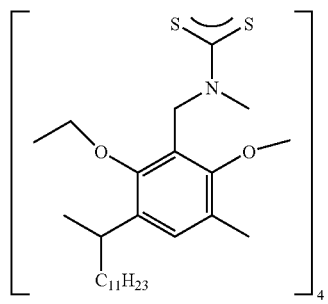

may be used to encapsulate surfaces that are nanoparticles.

The invention includes embodiments directed to methods for preparing ligands capable of molecular recognition. The surface-bound carbodithioate made according to methods of the invention may interact with the target molecular or biomolecular analyte to produce a response that can be sensed analytically. Analytical techniques used to sense the analyte may be optical or mass-based sensing. Examples of optical analytical techniques include surface plasmon resonance and surface enhanced raman scattering (SERS). Quartz crystal microbalance is a mass-based sensing technique. Thus, the surface-bound carbodithioate ligand acts as a recognition element. Such ligands may be stable under biologically relevant conditions.

In one embodiment of the invention, metal nanoparticles such as gold nanoparticles with specific plasmon resonances may be functionalized with carbodithioate-appended ligands according to the invention which, in turn, may have an affinity for biomolecular species such as peptides, small proteins, DNA, carbohydrates, oligonucleotides, and bioactive natural products. This functionalization may occur by passivating the nanoparticle with a mixture of a carbodithioate ligand not used for molecular recognition and a carbodithioate ligand capable of molecular recognition. Passivation can be extended with carbodithioates intended to block nonspecific protein adsorption, such as with di(hexaethyleneglycol) dithiocarbamate.

Examples of carbodithioates not used for molecular recognition include dimethyl dithiocarbamate, di(2-hydroxyethyl)-dithiocarbamate, and di(hexaethyleneglycol)-dithiocarbamate. Examples of carbodithioate ligands capable of molecular recognition include biotin, carbohydrates, oligopeptides, vitamin-derived moieties such as pteroate and folate, and synthetic metal ion receptors such as crown ethers and terpyridines. A particular example is N-(4-aminoterpyridinyl)-piperazinyl dithiocarbamate.

Carbodithioate ligands of the invention may be used to coat, for example, gold-coated substrates, such as those used in surface plasmon resonance (SPR) and quartz crystal microbalance (QCM) detectors, for high-throughput bioassays or pathogen detection.

The ligands used for biosensing applications of the instant invention are more stable than corresponding ligands made by prior art thiols due to the greater stability of the carbodithioate ligand-bonded surfaces of the invention. For example, under aqueous pH ranging from 1 to 12, a carbodithioate ligand of the invention, for example, reveals minimal changes to its spectral profile even after one week of immersion at ambient temperatures. Other stresses have similarly shown the carbodithioate ligands of the invention to be more stable than thiols bonded to surfaces.

"Functionalization" of a surface refers to the act of attaching carbodithioate ligands onto a substrate for the purpose of providing one or more specific functions, such as recognition by a complementary protein or cell-surface receptor, resistance against nonspecific protein adsorption, or generation or amplification of an optical signal or signature. Preferred surfaces of this embodiment include metal nanoparticles. A particularly preferred surface is a gold nanoparticle. Functionalization can be achieved by attaching a carbodithioate ligand which can support one or more of the functions above, and/or passivating the surface with a chemically or biologically inert ligand.

An inert ligand is one in which no appreciable chemical or biomolecular adsorption or reaction takes place as determined by a suitable analytical technique. Examples of carbodithioates which are likely to be biologically inert include di(2-hydroxyethyl)-dithiocarbamate and di(hexaethyleneglycol)-dithiocarbamate.

A functional ligand is one which is capable of specific activity and/or molecular recognition. Examples of ligands which have been attached to surfaces as carbodithioates and are capable of biological function or recognition include folate and pteroate derivatives, biotin hydrazide, carbohydrates and oligosaccharides, and cell-penetrating oligopeptides.

Molecular recognition events may be determined with a suitable analytical technique such as SERS or SPR. Upon a binding event, SERS spectra will show a characteristic peak or a change in peak frequencies based on the ligand, surface, and molecular analyte used. Alternatively, one may use SERS difference spectroscopy or a combination of SERS, SERS difference spectroscopy or a combination thereof.

Because of the strong affinity carbodithioate ligands have for surfaces of the invention, such as gold nanoparticles, such ligands are particularly suited for functionalizing SERS-active sites.

In another embodiment of the invention, methods for preparing core-shell materials comprising encapsulating a nanomaterial with a carbodithioate ligand are provided. In this embodiment, the encapsulated nanomaterial may be prepared according to the invention. It is extracted into an organic solvent such as a nonpolar solvent. Examples of non-polar solvents include toluene, dichloromethane, and dichlorobenzene.

The extracted and encapsulated nanomaterial is treated with an organometallic compound to form a core-shell nanomaterial. Examples of organometallic compounds include $Fe(CO)_5$ and $Fe(acetylacetonate)_3$. The nanomaterial may be heated to temperatures over 200° C.

The resulting core-shell material contains a metal or metal oxide shell, which derives from the organometallic compound, around the nanomaterial which may be a nanoparticle or a nanorod. Preferred nanoparticles and nanorods are gold. If iron is used as the metal in the organometallic compound, the nanorod will be magnetic and will produce a strong absorption in the NIR region. Such core-shell nanomaterials could be used as contrast agents for biomedical imaging applications.

In a yet another embodiment of the invention, methods for preparing imaging agents are provided wherein the surface of a nanoparticle is passivated and functionalized. In this embodiment, the nanoparticle surface is functionalized with a combination of biologically active nucleophiles and biologically inactive nucleophiles. Preferred nanoparticles of this embodiment are gold nanoparticles including gold nanorods. Optionally, the gold nanorod may be coated with a cationic surfactant such as cetyltrimethylammonium bromide. Other nanoparticles include CdSe and iron oxide.

Surface passivation may occur by exchanging the surfactant molecules using standard chemical techniques with carbodithioate ligands. This may be achieved, for example, by condensing a sulfur-containing compound and a nucleophile in a suitable solvent onto the nanoparticle thereby forming a carbodithioate ligand. A preferred sulfur-containing compound is $CS_2$, a preferred nucleophile is oligo(ethyleneglycol)amine, and water is a preferred solvent.

Biologically inert ligands are those that do not interact appreciably with biomolecular species whereas biologically active ligands provide the basis for a positive detection of biomolecular species.

Examples of biologically inert ligands include oligo(ethyleneglycol)amines whereas biologically active ligands would be formed from amines conjugated to, for example, pteroate or folate ligands. For example, the folate receptor is known to be over expressed in many tumor cells. Thus, such biologically active ligands may be used to label tumor cells.

The term "alkyl" is intended to include linear, branched, or cyclic hydrocarbon structures and combinations thereof. Examples of alkyl groups include methyl, ethyl, propyl, isopropyl, butyl, s- and t-butyl and the like. Cycloalkyl is a subset of alkyl and includes cyclic hydrocarbon groups of from 3 to 13 carbon atoms. Examples of cycloalkyl groups include cyclopropyl, cyclobutyl, cyclopentyl, norbornyl, adamantyl, menthyl, and the like. As used herein, alkyl refers to alkanyl, alkenyl and alkynyl residues; it is intended to include cyclohexylmethyl, vinyl, allyl, isoprenyl and the like.

"Acyl" refers to a straight, branched or cyclic configuration of carbon atoms, typically from 1 to 20, or a combination of any such configurations, attached to the parent structure through a carbonyl functionality. Such acyl groups can be saturated or unsaturated, and aromatic or non-aromatic. One or more carbons in the acyl group may be substituted with nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like.

"Aryl" and "Heteroaryl" mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. Examples of aromatic compounds which may be used to form aryl or heteroaryl groups include benzene, naphthalene, indane, tetralin, fluorene, imidazole, pyridine, indole, thiophene, benzopyranone, thiazole, furan, benzimidazole, quinoline, isoquinoline, quinoxaline, pyrimidine, pyrazine, tetrazole and pyrazole.

"Biologically relevant conditions" means those conditions, such as temperature and pH, that would be found in biological fluids relevant for medical treatment or diagnostics. Such fluids include blood and gastrointestinal fluid.

"Molecular recognition" refers to the capacity of ligands (i.e., recognition elements) to bind analytes or other molecules including biomolecules such as proteins with high levels of specificity and/or avidity.

"Passivation" refers to the lowering of a surface's chemical reactivity toward nonspecific adsorption. This includes the adsorption of carbodithioate ligands which provide resistance against nonspecific protein adsorption.

"Stable" means that a carbodithioate ligand on a surface does not appreciably dissociate under biological conditions during the timespan of an analytical test design for sensing applications.

"Xanthates" means salts of xanthic acid of the general formula ROC(S)SH where R is alkyl. One typical xanthic acid is where R is ethyl.

The following examples illustrate several embodiments of the invention and in no way meant to be limiting.

Preparation of Chemical Reagents:

Spectrophotometric grade $CS_2$ (Sigma-Aldrich) was freshly distilled from $CaH_2$ just prior to use. Dimethylamine, diethylamine, dibutylamine, didecylamine, diisopropylamine, piperidine, and morpholine (Aldrich) were used without further purification. In the case of dimethylamine, neat samples could be obtained by condensation at $-78°$ C.

Roughened Au Substrates:

Au foil (0.1 mm, Alfa Aesar) was cut into 6×6 mm squares and annealed by a propane torch for 2-3 min, sonicated for 10 min in deionized water, then roughened using a potentiostat (Princeton Applied Research 273A) in 0.1 M KCl. The parameters for electrochemical roughening were as follows: (i) initial potential (E1) of $-0.3$ V, (ii) a delay time (D1) of 30 sec; (iii) ramping the potential at a rate of 500 mV/sec to an upper limit (E2) of 1.2 V; (iv) a delay time (D2) of 1.3 sec, (v) decreasing the potential at a rate of 500 mV/sec to E1. The oxidation-reduction process was repeated for 25 cycles, in accord with the protocol of Weaver and coworkers (J. Electroanal. Chem. 1987, 233, 211). All voltages were referenced against a saturated calomel electrode (SCE).

Smooth Au Substrates:

Thin glass cover slips (Corning, 18'18 mm$^2$) were coated with a 10-nm Cr adhesive layer and 50-nm Au film by thermal evaporation, and used immediately after preparation.

Double Layered Nanoporous Gold Leaf:

Gold leaf was treated in $HNO_3$ (70%) 30 min, then transferred to mercapto-modified glass slides. Samples were then heated at 110° C. for 30 min. Samples were treated in 10 mM $NaI/I_2$ for 20 min. Then transferred second layer of nanoporouse gold leaf was heated at 110° C. for 10 min and treated in 10 mM $NaI/I_2$ for 20 min. Colloidal Au nanoparticles in aqueous suspension (British Biocell International, EM.GC40, ~1011 particles/mL) were treated with a mixed-bed ion-exchange resin (Amberlite MB-3, Mallinckrodt) for 30 minutes to minimize the presence of electrolyte in solution.

EXAMPLE 1

Carbodithioate Ligands Formed on Au Surfaces

The ligands of FIG. 1 were readily formed by immersing gold substrates in solutions containing an equimolar ratio of $CS_2$ and the corresponding amine under slightly basic conditions, as well as by using a 2:1 ratio of $CS_2$ to amine. For example, a 10% solution of $CS_2$ in methanol (1 mL) was treated dropwise with one molar equivalent of secondary amine dissolved in the same solvent (1 mL), followed by vortex mixing for 30 sec. The final concentration of dithiocarbamate was 0.42 M. Au substrates were introduced and soaked for variable periods, then rinsed twice in pure methanol and dried in air. The structure of the corresponding amine can be derived by substituting a hydrogen from the —$CS_2$ moieties for each figure. Ligand 5, the tetradithiocarbamoyl derivative of tetra(N-methyl)aminomethyl resorcinarene, contains four —$CS_2$ units and the corresponding amine had four hydrogens in place of those units.

The reactions to form the ligands in FIG. 1 were performed separately in one-pot reactions where $CS_2$ and the amine corresponding to each structure were combined in water, methanol, ethanol, or mixtures thereof.

Contact angle measurements of carbodithioate-functionalized gold surfaces revealed marked changes in their wetting properties: smooth gold substrates coated with dimethyl dithiocarbamate (ligand 1) ($\theta_{av}=60°$) are more hydrophilic than bare gold ($\theta_{av}=80°$), whereas those coated with dibutyl and didecyl dithiocarbamates (see ligands 3 and 4) are more hydrophobic ($\theta_{av}=107°$ and 108°, respectively). By comparison, substrates treated with dialkylamines in the absence of $CS_2$ did not exhibit significant changes in wetting behavior after rinsing.

EXAMPLE 2

Gold Nanoparticles

Carbodithioates were assembled on colloidal gold nanoparticles by suspending aqueous suspensions of 40-nm Au particles treated with $CS_2$ and tetra(N-methyl)aminomethyl resorcinarene (TMAR) at millimolar concentrations. The aqueous suspension of Au colloid (1 mL) was treated with a mixed-bed ion-exchange resin (MB-3), then decanted and mixed vigorously with a 1 mM solution of $CS_2$ in THF (1 mL). A 1 mM solution of TMAR in THF (1 mL) was added, and the solution was agitated vigorously by vortex mixing for another 5 minutes. Addition of $CH_2Cl_2$ (1 mL) resulted in phase separation, with extraction of the nanoparticles to the organic phase. No extractions occurred in the absence of $CS_2$ or TMAR.

EXAMPLE 3

Characterization Studies

A carbodithioate assembly on a roughened Au substrate was further characterized using surface-enhanced Raman spectroscopy (SERS; see FIG. 2). The SERS spectra of ligands 1-4 of example 1, formed by in situ condensation of amines with $CS_2$, were found to be nearly identical with those generated from preformed dithiocarbamate sodium salts, thus providing confirmation of structure.

Vibrational modes were assigned according to density functional theory (DFT) calculations: Raman frequencies were calculated for ligands 1 and 2 bonded to a cluster of gold atoms (1-3 atoms) using the B3LYP method and LANL2DZ basis set. The calculated values correlated well with the experimental SERS data, most notably for peak frequencies at 430-450 $cm^{-1}$ (I) and 540-600 $cm^{-1}$ (II). These vibrational bands correspond with symmetrically coupled C—S stretching and N-alkyl bending (scissoring) modes of the carbodithioate moiety anchored to the metal surface (see FIG. 4). Moreover, the SERS bands at 1450-1475 $cm^{-1}$ associated with C—H bending modes increased in prominence with hydrocarbon chain length.

EXAMPLE 4

Robustness Studies

Roughened Au substrates functionalized with ligands 1 and others functionalized with ligand 2 were exposed to aqueous solutions ranging from pH 1 to pH 12 and monitored by SERS. The data revealed minimal changes in spectral profile after one week of immersion at ambient temperature. In a second instance, ligand-coated substrates were immersed for one week in ethanolic solutions of dodecanethiol, again with minimal perturbations to their SERS spectra.

A smooth Au surface coated with dibutyl dithiocarbamate (ligand 3) was exposed to a millimolar solution of 2-mercaptoethanol for 24 hours, a condition known to completely displace alkanethiol monolayers. Minimal change in contact angle was observed ($\Delta\theta_{av} < 3°$), and analysis by x-ray photoelectron spectroscopy (XPS) showed that the S:N mole ratio remained unchanged at 2.14 to 1. The limits of thermal stability under aqueous conditions were also examined, with a decrease in contact angle finally observed after 12 hours at 85° C.

EXAMPLE 5

Functionalization of SERS-Active Nanoporous Gold

A nanoporous gold substrate was prepared by etching white gold leaf in concentrated nitric acid, similar to the process described by Erlebacher and coworkers (*Adv. Mater.* 16, 1897-1900 (2004)). The nanoporous gold leaf was rinsed with deionized water, bonded onto a glass slide modified with mercaptopropyltrimethoxysilane, then further etched with iodine and potassium iodide to yield a substrate that was highly SERS-active at an excitation wavelength of 785 nm. Depositing a second layer of nanoporous gold leaf further increased the activity and reproducibility of the SERS signal intensities.

The substrate was then functionalized with carbodithioate ligands using a two-step process, on the premise that the SERS-active sites are recessed within the nanoporous substrate and are only functionalized at a late stage of the coating process. The first step involved passivating the substrate with simple carbodithioate ligands with no recognition capabilities. Carbodithioates used were dimethyl-dithiocarbamate, di(2-hydroxyethyl)-dithiocarbamate, and di(hexaethyleneglycol)-dithiocarbamate.

The ligand concentration and soaking period was optimized for maximum surface coverage without producing any vibrational signals related to the dithiocarbamate ligands themselves. The second step involved adding a molecular recognition ligand N-(4'-aminoterpyridinyl)-piperazinyl dithiocarbamate, which can serve as a synthetic receptor for Zn ions. A higher ligand concentration and a longer soak time was used to drive the ligands into the SERS-active sites. This two-step process ensures that the molecular analyte recognition should only occur at SERS-active sites. The molecular recognition event was detected by observation of a characteristic Raman signal, by SERS difference spectroscopy, or a combination thereof.

EXAMPLE 6

Prophetic Example of Synthesis of Core-Shell Nanomaterials

Calixarene-based multivalent dithiocarbamates may be used as surfactants, specifically when formed by the in situ condensation of $CS_2$ and Tetra(N-methyl)aminomethyl resorcinarene (TMAR) and can further be used to extract colloidal Au nanoparticles (40 nm) and Au nanorods (15×50 nm) into nonpolar organic solvents such as toluene and dichloromethane, which can then be transferred to other solvents such as dichlorobenzene. The superior surfactant properties of calixarenes and particularly resorcinarenes have been previously described for dispersing nanoparticles (Wei, A., *ChemComm*, 1581-1591 (2006); Wei, A.; Kim, B. "Nanoparticle Arrays and Sensors Using Same." U.S. Pat. No. 6,899, 947, issued May 31, 2005) which are incorporated herein by reference.

Nanorods encapsulated in TMAR-based DTC surfactants can be heated to over 200 degrees Celsius for short periods of time without degradation or precipitation. This dispersion control enables the synthesis of a core-shell nanomaterial. For example, an organometallic precursor (e.g., $Fe(CO)_5$ or $Fe(acetylacetonate)_3$) can be injected into the hot nanorod suspension at high temperatures to form an iron or iron-oxide shell around the nanorod core, producing a magnetically active nanorod with strong absorption in the NIR region.

EXAMPLE 7

Forming Functionalized Nanoparticles for use as Biological Imaging Agents

Gold nanorods coated with cetyltrimethylammonium bromide (CTAB, a cationic surfactant) can be passivated using simple surfactant exchange with DTC ligands, formed by in situ condensation of oligo(ethyleneglycol)amines with $CS_2$ in aqueous solutions. Surfaces comprised of such molecules are expected to resist nonspecific protein adsorption. The passivated nanorods can be purified by dialysis using a semipermeable membrane to remove excess surfactant. These nanorods are anticipated to be biologically inert and have a long circulation half-life, whereas CTAB-coated nanorods would be expected to be rapidly internalized via a nonspecific cell uptake mechanism. Iron oxide and CdSe nanoparticles are also amenable to functionalization with hydrophilic dithiocarbamate ("DTC") ligands, and can form stable suspensions in aqueous solutions.

Nanoparticles can be functionalized with biologically active ligands by sequential conjugation reactions. In one instance, a 1-mL suspension of gold nanorods (ca. $10^9$ particles) was treated with 8.8 mg of oligo(ethyleneglycol)diamine (n~18, ca. 28 μmol) and 100 μL of a saturated $CS_2$ solution (ca. 2.8 μmol) to produce carbodithioate ligand at an assumed final concentration of 2.8 mM. The mixture was stirred overnight, and the excess ligand was separated from the functionalized nanorods by dialysis using a cellulose membrane with MWCO of 6000-8000. The amine-coated nanorods were treated with 50 μL of a folate-NHS solution (10 mM in DMSO) with overnight stirring. The resulting folate-conjugated nanorods were separated from the excess folate by membrane dialysis.

EXAMPLE 8

Prophetic Example on Using Functionalized Ligands

Nanoparticles can be functionalized with biologically active ligands at controlled densities using a binary surfactant system. In one instance, oligo(ethyleneglycol)amines conjugated with pteroate or folate ligands can be combined with inert oligo(ethyleneglycol)amines in the presence of $CS_2$, then introduced to nanoparticles with the expectation that their surfaces will be completely passivated by carbodithioate units, with a statistical ratio of biologically active and inert ligands. This stoichiometric control is useful for tuning the binding avidity of nanoparticles; for example, the surface density of folate ligands can be optimized for labeling tumor cells which over express the folate receptor, while minimizing adventitious binding to healthy cells which display a normal level of this surface protein.

EXAMPLE 9

Carbodithioate Formation by $CS_2$ and Biotin Hydrazide on Gold Surface

5 μL $CS_2$ was dissolved in 0.5 mL DMSO. 5.4 mg biotin hydrozide was dissolved in 0.5 mL DMSO, and added to $CS_2$ solution dropwise under stirring. Au substrates were introduced and soaked for 10 minutes, then rinsed twice in pure methanol and dried in air.

The invention claimed is:

1. A method for preparing a surface for use as a biosensor, comprising:
    forming a carbodithioate ligand by mixing $CS_2$ with a nucleophile represented by formula $NHR^1R^2$ in the presence of a solvent selected from the group consisting of methanol, ethanol, n-propyl alcohol, isopropyl alcohol, water, toluene, dichloromethane, dichlorobenzene and combination thereof and
    immersing the surface in the mixture to cause the carbodithioate ligand to bond thereto, the surface being selected from at least one of a Group 13 metal, a Group 14 metal, a Group 15 metal, iron oxide, cadmium selenide, cadmium sulfide, indium tin oxide and gold;
    wherein the formed carbodithioate ligand is represented by the structure $R^1R^2N—CS_2$;
    wherein $R^1$ and $R^2$ are independently selected from —H, alkyl, acyl, aryl, heteroaryl, —$OR^3$, —$NR^4R^5$, $SiR^6R^7R^8$ or $SR^9$;
    $R^3$, $R^4$, $R^5$, $R^6$, $R^7$, and $R^8$ are independently selected from —H, alkyl, acyl, aryl, or heteroaryl; and
    $R^9$ is aryl or heteroaryl.

2. The method of claim 1 wherein the nucleophile is an amine.

3. The method of claim 2 wherein the amine is a primary amine, a secondary amine, a heterocyclic amine, or a silyl amine.

4. The method of claim 1 wherein the nucleophile is a primary amide or a secondary amide.

5. The method of claim 1 wherein the nucleophile is selected from the group consisting of dimethylamine, diethylamine, diisopropylamine, dibutylamine, didecylamine, dipicolylamine, diethanolamine, di(hexaethyleneglycol)amine, morpholine, pyridine, praline, oligopeptides bearing N-terminal prolines, piperazinyl terpyridine, nortriptylene, methamphetamine, reductive amination products of oligosaccharides with primary amines, biotin hydrazide, hexamethyldisilazane, and oligo(ethyleneglycol)diamines conjugated to molecular recognition elements such as folic acid or pteroic acid.

6. The method of claim 1 wherein the surface-bound carbodithioate is chemically stable and resistant to surface desorption or displacement when exposed to a condition that has a temperature and a pH value characteristic of blood or gastrointestinal fluid.

7. A method for preparing a surface for use as a biosensor, comprising:
    forming a carbodithioate ligand by mixing $CS_2$ with a nucleophile in the presence of a suitable solvent, the nucleophile being selected from the group consisting of dimethylamine, diethylamine, diisopropylamine, dibutylamine, didecylamine, dipicolylamine, diethanolamine, di(hexaethyleneglycol)amine, morpholine, pyridine, praline, oligopeptides bearing N-terminal prolines, piperazinyl terpyridine, nortriptylene, methamphetamine, reductive amination products of oligosaccharides with primary amines, biotin hydrazide, hexamethyldisilazane, and oligo(ethyleneglycol)diamines conjugated to molecular recognition elements such as folic acid or pteroic acid; and
    immersing the surface in the mixture to cause the carbodithioate ligand to bond thereto, the surface being selected from the group consisting of a Group 13 metal, a Group 14 metal, a Group 15 metal, iron oxide, cadmium selenide, cadmium sulfide, indium tin oxide and gold;
    wherein said solvent is selected from the group consisting of methanol, ethanol, n-propyl alcohol, isopropyl alcohol, water, toluene, dichloromethane, dichlorobenzene and combination thereof.

8. The method of claim 7, wherein the surface-bound carbodithioate is chemically stable and resistant to surface desorption or displacement when exposed to a condition that has a temperature and a pH value characteristic of blood or gastrointestinal fluid.

* * * * *